(12) United States Patent
Cracknell et al.

(10) Patent No.: US 10,399,997 B2
(45) Date of Patent: Sep. 3, 2019

(54) PROCESS FOR PREPARATION OF 3-METHACRYLOXYPROPYLDIMETHYL CHLOROSILANE IN CONTINUOUS FLOW REACTOR

(71) Applicant: GEO SPECIALTY CHEMICALS UK LIMITED, Bristol (GB)

(72) Inventors: Robert Cracknell, Bristol (GB); Melissa Matthews, Bristol (GB); Andrew Small, Bristol (GB); Adam Barter, Teesside (GB)

(73) Assignee: Geo Specialty Chemicals UK Limited (GB)

( * ) Notice: Subject to any disclaimer, the term of this patent is extended or adjusted under 35 U.S.C. 154(b) by 116 days.

(21) Appl. No.: 15/324,740

(22) PCT Filed: Jul. 9, 2015

(86) PCT No.: PCT/GB2015/051992
§ 371 (c)(1),
(2) Date: Jan. 9, 2017

(87) PCT Pub. No.: WO2016/005757
PCT Pub. Date: Jan. 14, 2016

(65) Prior Publication Data
US 2017/0197995 A1    Jul. 13, 2017

(30) Foreign Application Priority Data
Jul. 11, 2014    (GB) .................................. 1412406.9

(51) Int. Cl.
| C07F 7/12 | (2006.01) |
| C08G 77/20 | (2006.01) |
| C08G 77/38 | (2006.01) |
| B01J 19/24 | (2006.01) |
| B01J 31/16 | (2006.01) |
| C07F 7/08 | (2006.01) |

(52) U.S. Cl.
CPC .............. *C07F 7/122* (2013.01); *B01J 19/24* (2013.01); *B01J 31/1608* (2013.01); *C07F 7/0838* (2013.01); *C07F 7/12* (2013.01); *C08G 77/20* (2013.01); *C08G 77/38* (2013.01); *B01J 2219/00033* (2013.01); *B01J 2231/323* (2013.01); *B01J 2531/828* (2013.01)

(58) Field of Classification Search
CPC ........... C07F 7/122; C07F 7/12; C07F 7/0838
USPC ...................................................... 556/479
See application file for complete search history.

(56) References Cited

U.S. PATENT DOCUMENTS

| 3,258,477 | A |   | 6/1966  | Plueddemann et al. |
| 4,276,426 | A | * | 6/1981  | Lindner ................. C07F 7/0879 556/479 |
| 4,709,067 | A |   | 11/1987 | Chu et al. |
| 4,780,555 | A | * | 10/1988 | Bank ....................... C07F 7/121 556/401 |
| 5,262,555 | A |   | 11/1993 | Okawa et al. |
| 5,359,113 | A |   | 10/1994 | Bank |
| 5,493,039 | A |   | 2/1996  | Okawa et al. |
| 5,550,272 | A |   | 8/1996  | Lewis et al. |
| 5,578,278 | A | * | 11/1996 | Fall ....................... B01J 19/2435 422/129 |
| 5,646,325 | A |   | 7/1997  | Monkiewicz et al. |
| 5,811,565 | A |   | 9/1998  | Mikami et al. |
| 5,824,195 | A |   | 10/1998 | Kimae et al. |
| 5,847,178 | A |   | 12/1998 | Okawa |
| 5,914,418 | A |   | 6/1999  | Mikami et al. |
| 6,013,822 | A |   | 1/2000  | Okawa |
| 9,695,093 | B2 | * | 7/2017 | Shekarriz ................. C10L 5/445 |
| 2007/0004930 | A1 |   | 1/2007 | Onodera et al. |
| 2010/0179340 | A1 | * | 7/2010 | Lang .................... B01J 19/0093 556/437 |
| 2011/0237766 | A1 |   | 9/2011 | Maggio et al. |

FOREIGN PATENT DOCUMENTS

| CN | 101157700 |   | 4/2008 |
| CN | 101157700 | A | 4/2008 |
| GB | 949126 |   | 2/1964 |
| JP | S604193 | A | 1/1985 |
| JP | H10-158282 | A | 6/1998 |
| JP | 2003-96086 | A | 4/2003 |
| JP | 2004-285020 | A | 10/2004 |
| WO | WO 2008/017555 | A1 | 2/2008 |

OTHER PUBLICATIONS

Judith Stein, et al., In Situ Determination of the Active Catalyst in Hydrosilylation Reactions Using Highly Reactive Pt(0) Catalyst Precursors, J. Am. Chem. Soc., vol. 121, No. 15. 1999, pp. 3693-3703.

* cited by examiner

*Primary Examiner* — Margaret G Moore
(74) *Attorney, Agent, or Firm* — Brinks Gilson & Lione; Ryan L. Marshall; Jonathan Hartley

(57) ABSTRACT

A process for the preparation of 3-methacryloxypropyldimethylchlorosilane by reaction of allylmethacrylate with dimethylchlorosilane in the presence of a hydrosilylation catalyst, characterized in that the reaction is carried out in the absence of a peroxide is provided. The process includes providing a first stream containing allylmethacrylate. A a second stream containing dimethylchlorosilane is provided. The streams contact in a continuous flow reactor in the presence of the hydrosilylation catalyst, thereby producing 3-methacryloxypropyldimethylchlorosilane. A product stream is continuously removed from the continuous flow reactor.

18 Claims, 1 Drawing Sheet

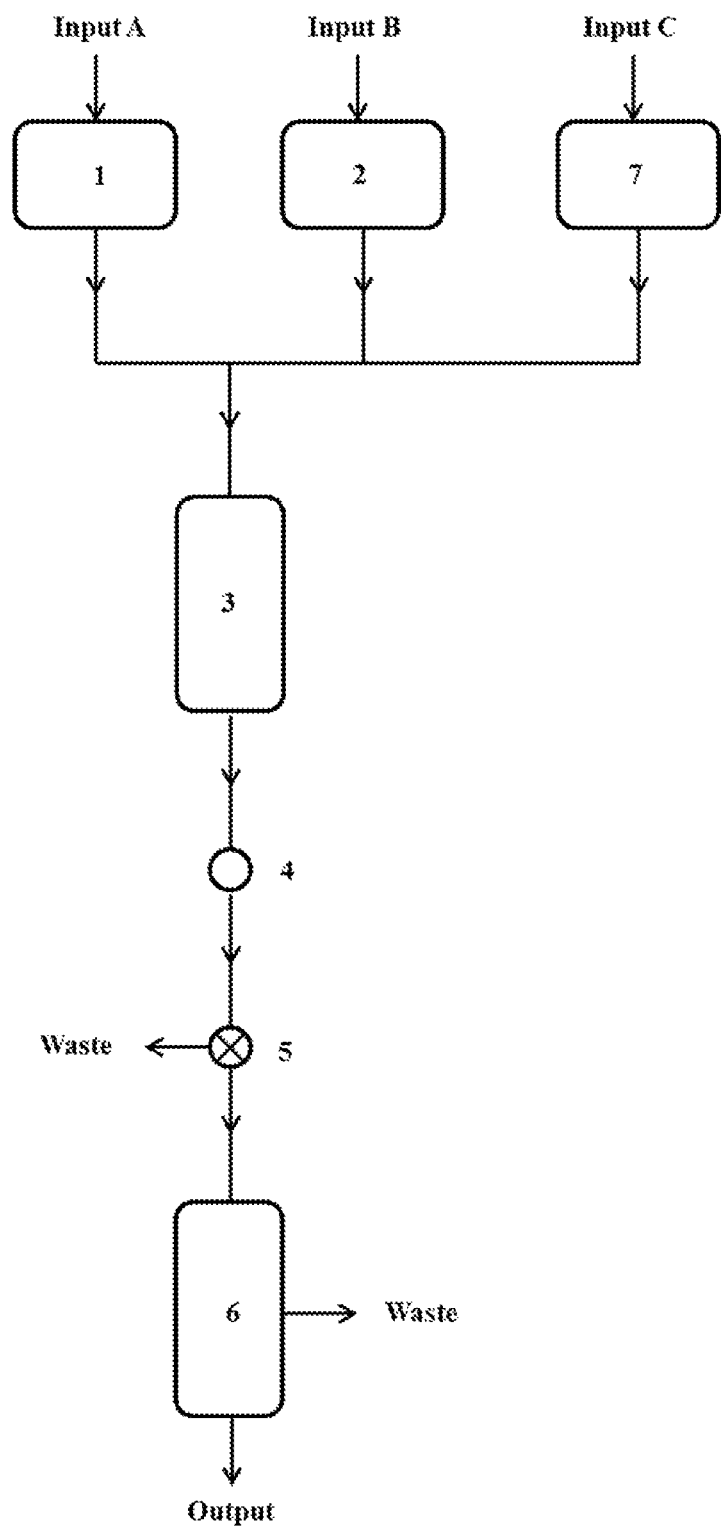

PROCESS FOR PREPARATION OF 3-METHACRYLOXYPROPYLDIMETHYLCHLOROSILANE IN CONTINUOUS FLOW REACTOR

CROSS-REFERENCE TO RELATED APPLICATIONS

This application is a filing under 35 U.S.C. 371, which claims priority to International Application Serial No. PCT/GB2015/051992, filed Jul. 9, 2015, which application claims a right of priority to Great Britain Patent Application No. 1412406.9, filed Jul. 11, 2014, both of which are incorporated herein by reference in their entirety.

TECHNICAL FIELD

The present disclosure relates to a process for the preparation of 3-methacryloxypropyl-bisdimethylchlorosilane (MOPDMCS).

BACKGROUND

The synthesis of organosilicon compounds by reaction of an organic compound containing an alkenyl group with a hydrosilane, resulting in addition of silicon and hydrogen across the carbon-carbon double bond of the alkenyl group, is well known. The general method, usually carried out in the presence of a transition metal catalyst, has been known for many decades. It has generally been believed that continuous processes are not suitable for the production of acryloyl- or methacryloyl-organosilicon compounds using hydrosilation catalysts, for a number of different reasons. First, it would be expected that polymerization would occur and would disrupt the flow process; second, an induction period is required for catalyst activation, and this would be expected to mean that a continuous process would not work; and third, deactivation of the catalyst is known to occur over time. U.S. Pat. No. 5,359,113 describes this latter problem, which it believes is caused by lack of oxygen, and solves the problem by adding a peroxide into the hydrosilylation reaction. Using MeHSiCl$_2$ as the silane and allyl chloride as the unsaturated compound, Comparative Example 1 of U.S. Pat. No. 5,359,113 illustrates catalyst deactivation during a continuous reaction process, while Example 1 shows that addition of a peroxide avoids this problem, permitting the use of a continuous reaction process. However, the reaction of U.S. Pat. No. 5,359,113 cannot in practice be used for the preparation of acryloyl- or methacryloylsilicon compounds because peroxide is a known initiator for polymerization. Even without the addition of peroxide, it is known that polymerization causes major problems in known processes for the preparation of acryloyl- or methacryloylsilicon compounds.

3-Methacryloxypropyl-bisdimethylchlorosilane (MOPDMCS) is a key raw material for the manufacture of methacryloxy propyl dimethyl methoxysilane (mPDMS), which is used in the manufacture of contact lenses. MOPDMCS is manufactured by the reaction of allyl methacrylate (AMA) and dimethylchlorosilane (DMCS) in the presence of a transition metal hydrosilylation catalyst, usually based on platinum.

However, known processes for the preparation of MOPDMCS suffer from a number of disadvantages, MOPDMCS being a particularly difficult methacryloyl organosilicon compound to prepare and handle. Controlling the process is difficult, and it is difficult to ensure batch-to-batch consistency. As a result, problems arise, in particular relating to product consistency and purity. For example, hydrolysis and dimerisation of the product occurs readily. Further, the product may form homopolymers, or it may copolymerize with by-products present in the reaction mixture. Such reactions can occur at any time during the preparative process and also during purification of the product, which may for example be carried out by distillation. It is thus difficult to prepare MOPDMCS having a high degree of purity.

Much research has been carried out to develop methods which reduce degradation of the product during or after preparation, either by reducing the content of by-products obtained, or by reducing the dimerization or polymerisation of the product. For example, U.S. Pat. No. 5,550,272 and EP 803507 describe the use of free radical polymerization inhibitors. U.S. Pat. No. 5,847,178 proposes adding copper compounds to the reaction mixture. EP 775,708 describes treatment of the reaction mixture with an inorganic chloride, while U.S. Pat. No. 5,811,565 describes treatment of the reaction mixture with a Lewis acid. EP 693492 describes carrying out the synthesis under low water conditions to minimize polymerization. EP 562584, WO 2004/085446 and EP 753521 describe additives to be used during purification of the product by distillation, aiming to reduce polymerization.

These known processes are all carried out using conventional batch processing techniques, and none of them addresses one major problem which contributes to batch-to-batch inconsistency, which is that the reaction has a long induction time during which activation of the catalyst takes place. Not only is the induction time long, but it is unpredictable, varying significantly from batch to batch. Generally, if reactants are added during the induction period, they will accumulate, and once the reaction begins, large quantities of heat are generated and the temperature will rise to an undesired level. Under these circumstances, runaway reactions and polymerization are likely to occur. Even if steps are taken to monitor and deal effectively with the induction period, batch-to-batch consistency tends to be low.

US 2010/179340 describes some of the disadvantages of batch processes for the preparation of methacryloyloxypropylalkoxysilanes, and describes a continuous process for the preparation of methacryloylorganosilicon compounds by the reaction of allyl methacrylate with a hydrosilane using a specific system of reactors. The hydrosilanes used in the process are alkoxyhydrosilanes. WO 2008/017555 contains a very similar disclosure to US 2010/179340, and as for US 2010/179340, the example of preparing a methacryloxy compound is carried out using a methoxysilane.

Methacryloylalkoxysilanes of the type prepared in US 2010/179340 and WO 2008/017555, and the alkoxyhydrosilanes used to make them, are known to be relatively stable and easy to handle compared with other hydrosilanes. Specifically, a reaction mixture including AMA, a platinum hydrosilylation catalyst and DMCS would be expected to have a much greater propensity to form by-products and/or polymerise during synthesis than the corresponding reaction mixture including trimethoxysilane. MOPDMCS is particularly difficult to synthesise, due to its propensity to polymerise. It is believed that this is because Si—Cl bonds are highly susceptible to hydrolysis leading to the formation of hydrochloric acid, which catalyses both further decomposition and polymerization of any methacrylate bonds present. Because of its instability, MOPDMCS is always sold containing a significant level of polymerization inhibitors, typically from 100-200 ppm BHT plus 200-400 ppm MeHQ. In contrast, the corresponding 3-methacryloxypropyltrimethoxysilane (MOPTMOS) is sold with a very low level of polymerization inhibitor, typically less than 10 ppm BHT. The skilled person would not have expected that a continuous process for the preparation of MOPDMCS could be carried out successfully.

There remains a need for improved processes for the production of MOPDMCS. We have now found a highly efficient process which permits their preparation with high yield, as well as a high degree of consistency and purity. This is particularly surprising given the highly reactive nature of the reactants and product, and in particular their propensity to react with themselves and each other.

SUMMARY

Embodiments of the present disclosure provide a process for the preparation of methacryloxypropylbisdimethylchlorosilane by reaction of allyl methacrylate with dimethylchlorosilane in the presence of a hydrosilylation catalyst, characterized in that the reaction is carried out in the absence of a peroxide by a process comprising:
 i. providing a first stream containing allyl methacrylate;
 ii. providing a second stream containing dimethylchlorosilane;
 iii. contacting said streams in a continuous flow reactor in the presence of said hydrosilylation catalyst, thereby producing methacryloxypropylbisdimethylchlorosilane; and
 iv. continuously removing a product stream from said continuous flow reactor.

In a particularly preferred embodiment, the product stream is processed in an additional step v) which comprises carrying out a batch distillation of the product stream.

The surface area/volume ratio of the continuous flow reactor is an important parameter. Preferably it is from 4:1 to 400:1. The ratio of the path length of the reactants within the reactor to the cross sectional area of the reactor is also an important parameter. Preferably it is from 0.01:10,000 to 100:10,000. The reactor may take any desired form. Suitably it contains elongated channels having dimensions as above. These channels may have any desired cross-section, for example rectangular or circular.

Preferably, the process of the present disclosure is carried out in the absence or substantial absence of solvent. Surprisingly the process of the disclosed embodiments remains effective in consistently producing MOPDMCS in high yield and purity even under essentially solvent-free conditions.

Preferably, the process of the present disclosure comprises analysing the product stream produced in step (iii) for the presence and/or level of MOPDMCS and/or an impurity, more preferably the process comprises carrying out in-line analysis of the product stream. Analysing/monitoring the product stream permits a determination to be made regarding whether the product stream is of acceptable purity and/or yield, and processing conditions may be altered in response to that determination. For example, depending on whether a positive or negative determination is made, the product stream may be permitted to flow into a first receptacle containing crude product of acceptable purity, or may be diverted into a second receptacle containing crude product of unacceptable purity. Process conditions (e.g. temperature) may for example be adjusted in order to improve product purity and/or yield, or the continuous flow reactor purged, in response to a negative determination.

Preferably, the feed streams are provided to the continuous flow reactor at a flow rate such that they are contacted in the continuous flow reactor at a pressure in the range of from 1 to 100 bar (100 to 10,000 kilopascals). The use of such conditions results in the production of the acryloyl- or methacryloyl-organosilicon compound in particularly high yield and purity.

BRIEF DESCRIPTION OF THE DRAWINGS

FIG. 1 is a schematic flow diagram illustrating a preferred embodiment of the process of the present disclosure.

DETAILED DESCRIPTION

MOPDMCS has the formula:

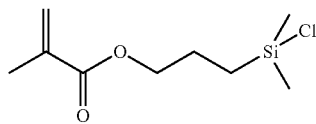

It has a number of different uses. Specifically, it may be used to synthesize silicone containing monomers, for example for use in contact lens formulations which on curing produce lenses with high oxygen permeability.

In step (i) of the process of the present disclosure, a first stream containing AMA is provided. As discussed above, reaction of the AMA with DMCS results in addition of silicon and hydrogen across the carbon-carbon double bond.

The first stream may if desired include an organic solvent, for example an aromatic hydrocarbon such as benzene, toluene or xylene; an aliphatic hydrocarbon such as hexane or heptane; an ether such as tetrahydrofuran or diethyl ether; a ketone such as acetone or methyl ethyl ketone; or an ester such as ethyl acetate or butyl acetate. Preferably however no solvent is present other than, if desired, the quantities of solvent required to deliver the hydrosilylation catalyst if said catalyst forms part of said first stream as described below. In step (ii) of the process of the present disclosure, a second stream containing dimethylchlorosilane is provided.

Said second stream may if desired include an organic solvent, for example one of the solvents mentioned above for the first stream. It may for example include up to 20% of solvent. However, preferably no solvent is present other than, if desired, the quantities of solvent required to deliver the hydrosilation catalyst if said catalyst forms part of said second stream as described below.

Step (iii) is carried out in a continuous flow reactor. The surface area/volume ratio of the reactor is an important parameter. Preferably it is from 4:1 to 400:1, for example 10:1 to 200:1, particularly 20:1 to 100:1. Within the reactor, said first and second streams are contacted in the presence of a hydrosilylation catalyst. The first and second streams may be introduced as separate streams into the reactor, or they may be combined immediately prior to entry to the reactor.

The catalyst may be introduced as part of the first stream, or as part of the second stream, or in a third stream which may be introduced directly into the continuous flow reactor or merged into either or both of the first or second streams immediately prior to entry into the reactor; or it may be pre-introduced into the continuous flow reactor. Preferably it is introduced as part of the first or second streams, more preferably as part of the first stream. Introducing the catalyst to the reactor as part of one of these streams ensures consistent production of product in high yield.

The optimum residence time in the reactor will depend upon the precise details of the reaction being carried out, but preferably the residence time is from 1 sec to 30 minutes, for example 10 sec to 15 minutes, preferably from 1 to 5 minutes. This brief residence time provides an advantage in using the process of the present disclosure in that the formation of by-products is minimized. Generally, the flow through the continuous flow reactor will be such that there is minimal spare head-room in the reactor.

Any suitable hydrosilylation catalyst may be used. Preferably the catalyst contains a transition metal. The catalyst may be homogeneous or heterogeneous. In one preferred embodiment, the catalyst is a homogeneous catalyst. Such catalysts may for example be based on rhodium, for example $RhCl_3$ or $Rh(PPh_3)_3Cl$ (where Ph is a phenyl group), or platinum. Platinum catalysts may be provided as chloroplatinic acid, platinum-olefin complexes, and complexes of platinum and vinyl-functional siloxane. Specific catalysts including Speier's catalyst ($H_2PtCl_6$ in i-PrOH), Karstedt's catalyst (the reaction product of $H_2PtCl_6$ and divinyltetramethyldisiloxane), Ashby's catalyst (the reaction product of $H_2PtCl_6$ and tetravinyltetramethyldisloxane) and Lamoreoux's catalyst ($H_2PtCl_6$ in n-octanol). The use of Karstedt's catalyst forms one preferred embodiment of the present disclosure. Generally, a homogenous catalyst will be provided in the form of a solution in an organic solvent, for example a solution in a polydimethylsiloxane or a hydrocarbon solvent, for example a xylene, hexane, heptane or toluene. If a heterogeneous catalyst is used, this may if desired be introduced into the continuous flow reactor prior to introduction of the first and second streams. As an example of a heterogeneous catalyst, there may for example be mentioned a solid-supported platinum catalyst, or a solid Cu(II) salt catalyst. Generally, the catalyst will be used in an quantity similar to, or a little lower than, the quantity used in known batch reactions. The use of rather lower quantities than in known reactions provides a further advantage of the process of the present disclosure, as the presence of lower quantities of catalyst would be expected to increase the stability of the product.

Step (iii) of the process of the present disclosure may be carried out at any desired temperature, for example at room temperature or an elevated temperature. Preferably the maximum temperature is kept below 200° C., especially below 120° C., in order to minimize polymerization or other undesired side reactions. For example the reaction temperature may be in the range of from 30 to 120° C., for example from 60 to 120° C., especially from 80 to 100° C. In a preferred embodiment of the process of the present disclosure, the reaction conditions including temperature, pressure and flow rates are controlled in such a way that the reaction temperature can be kept within these ranges, without causing vaporization of the hydrosilane. For example, DMCS can be handled at reaction temperatures of around 80° C. without any vaporization leading to optimum process efficiency.

Step (iii) of the process of the present disclosure may be carried out at atmospheric pressure but it is preferably carried out at elevated pressure as this assists in keeping all the components in the liquid phase and helps to achieve a consistent residence time. In one preferred embodiment, the streams are provided to the continuous flow reactor at a flow rate such that they are contacted in the continuous flow reactor at a pressure of up to 100 bar (10,000 kPa), for example a pressure in the range of from 1 to 100 bar (100 to 10,000 kPa), for example up to 70 bar (7,000 kPa), for example up to 50 bar (5,000 kPa). As discussed above, contacting the streams in the continuous flow reactor at such pressure leads to particularly high yields and purity of the MOPDMCS. However, lower pressures, for example up to 25 bar (kPa), especially up to 15 bar (kPa) may also be used, and these may provide advantages. Generally, a back pressure regulator will be provided at the end of the system, and this together with the applied pressure caused by the rate at which the streams are provided to the continuous flow reactor, and the pressure drop across the system, will determine the pressure in the continuous flow reactor.

The molar ratio of AMA to DMCS is not critical, but preferably approximately equivalent amounts, or a small excess of AMA, are used. For example, the molar ratio of AMA to DMCS may be in the range of from 1:1 to 1.5:1, for example 1:1 to 1.2:1.

As mentioned above, in a preferred embodiment, the first and second streams contain no added solvent other than if desired the small quantity of solvent required for provision of the catalyst. In one preferred embodiment, less than 20 wt %, preferably less than 10 wt % of the inputs to the continuous flow reactor are solvent. For example, less than 5 wt %, less than 4 wt %, less than 3 wt %, less than 2 wt %, less than 1 wt %, less than 0.5 wt % or less than 0.2 wt % of the inputs to the continuous flow reactor are solvent. In one preferred embodiment, at least 90 wt %, at least 95 wt %, at least 96 wt %, at least 97 wt %, at least 98 wt %, at least 99 wt %, at least 99.5 wt %, or at least 99.8 wt % of the inputs to the continuous flow reactor are the sum wt % of i) hydrosilylation catalyst, ii) DMCS, and iii) AMA.

Any known polymerization inhibitor may be present in step (iii) if desired. Suitable inhibitors include phenols, amines (for example N,N-diphenyl-p-phenylenediamine, DPPD), quinones and other oxygen-containing compounds, and copper salts, for example $Cu(I)O$, $Cu_2(I)(SO_4)$, $Cu(I)OH$, $Cu(I)Cl$, $Cu(I)OAc$ and $Cu(II)O$, $Cu(II)SO_4$, $Cu(II)(OH)_2$, $Cu(II)Cl_2$ and $Cu(II)(OAc)_2$, as well as those inhibitors disclosed in the prior art mentioned above. The use of a phenol, for example p-methoxyphenol, 4-hydroxyanisole, dibutylhydroxytoluene or bis(tert butyl)-4-methylphenol (BHT), or phenothiazine (PTZ), is preferred. Mixtures of inhibitors may be used. The inhibitor may be introduced as part of the first stream, or as part of the second stream, or it may be introduced into the continuous flow reactor by any other means, for example in a third stream. Preferably it is introduced as part of the first stream.

In batch reactions for the preparation of MOPDMCS, catalyst activation and hence an induction period is generally necessary. In known processes, catalyst induction issues can produce major problems, including significant inconsistencies between batches leading to reduced product purity. In the process of the present disclosure, it has surprisingly been found that no allowance needs to be made for activation of the catalyst. If desired, the flow through the continuous flow reactor in step (iii) can, during an initial start-up phase, be diverted to a waste stream. Once the catalyst is fully activated, collection of product can begin. Generally, however, such steps are not necessary.

Conveniently, the process of the present disclosure is controlled by analyzing/monitoring output from the reactor, specifically by analyzing/monitoring the crude product stream, using any suitable analytical technique, for example HPLC, GC-FID, GC-MS or, especially, IR, ideally using an in-line monitor. Such monitoring gives real-time information on accumulation of product and reaction activity, which leads to significant safety advantages, without the need for sampling and holding, leading to delays. It is advantageous to provide, in association with the monitoring, automated switching of the product stream to a waste stream in the event of sub-standard product, which in turn prevents contamination of any product collected prior to a problem arising.

Furthermore, during processing of MOPDMCS, polymerization events can occur, affecting the quality of the product obtained. Carrying out analysis of the product stream as it is produced permits early detection of such events, so that processing conditions may be altered if required. Accordingly, as discussed above, in one preferred embodiment the process of the present disclosure comprises analysing the product stream for the presence and/or level of MOPDMCS and/or an impurity, more preferably the process comprises carrying out in-line analysis of the product stream, yet more preferably the process comprises carrying out in-line IR analysis of the product stream.

In one preferred embodiment, the process of the present disclosure comprises determining the yield of MOPDMCS present in the product stream by carrying out in-line IR analysis and, where the yield of MOPDMCS is equal to or greater than a pre-defined value (e.g. at least 60%, at least 65%, at least 70%, at least 75%, at least 80% or at least 85%), passing the product stream to a first vessel; or, where the yield of MOPDMCS is less than said pre-defined value (e.g. at least 60%, at least 65%, at least 70%, at least 75%, at least 80% or at least 85%), passing the product stream to a second waste vessel.

Where in-line monitoring indicates that the yield/level of MOPDMCS is below a desired level, or where the level of an impurity is above a desired level, it may be desirable to adjust the process conditions in response in order to achieve an acceptable yield and/or purity of MOPDMCS in the product stream. For example, the temperature and/or flow rates of the first and/or second stream may be adjusted in response to a determination that the yield is less than a pre-defined value.

Furthermore, where in-line analysis/monitoring leads to a determination that the yield and/or purity of MOPDMCS in the product stream is unacceptable, in particular where a polymerization event is detected, it may be desirable to purge the continuous flow reactor, for example by stopping flow of the product stream to a first vessel and diverting it to a second waste vessel, passing a stream containing solvent and/or polymerization inhibitor through the continuous flow reactor in place of the first and second streams for a period of time (e.g. for at least 1, 2, 5, 10, or 20 minutes), before reverting to providing the original streams to the continuous flow reactor, and reverting to passing the product stream to the first vessel.

Following step (iii) of the process, a product stream is removed from the continuous flow reactor. If desired, this product stream may be subject to a purification step. For example, the product may be purified by a solvent extraction process or, preferably, distillation. In one preferred embodiment of the present disclosure, the product stream obtained by step iv) is subjected to a batch distillation process. Surprisingly, the use of batch distillation has proved to be an improvement over the use of continuous distillation, which would not be expected for a process in which step iii) is carried out in a continuous flow reactor. Accordingly, a preferred embodiment of the process of the present disclosure comprises a process for the preparation of MOPDMCS by reaction of AMA with DMCS in the presence of a hydrosilylation catalyst, characterized in that the reaction is carried out in the absence of a peroxide by a process comprising:
  i. providing a first stream containing AMA;
  ii. providing a second stream containing DMCS;
  iii. contacting said streams in a continuous flow reactor in the presence of said hydrosilylation catalyst, thereby producing MOPDMCS;
  iv. continuously removing a product stream from said continuous flow reactor; and
  v. subjecting said product stream to a batch distillation process.

Distillation may be carried out under known conditions, for example at a pressure of 0.1-10, preferably 1 to 5, mbar, and a temperature of 50-150. Preferably the distillation temperature is at least 60° C., for example at least 70° C., and preferably it is no greater than 120° C. It may for example be 60-120° C., for example 60-100° C. During this step, a polymerization inhibitor may be present if desired. Preferred inhibitors are as mentioned above.

The reaction of the present disclosure takes place by the following scheme:

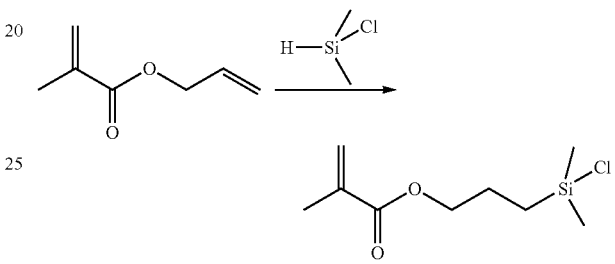

As mentioned above, MOPDMCS can for example be converted into compounds of the formulae:

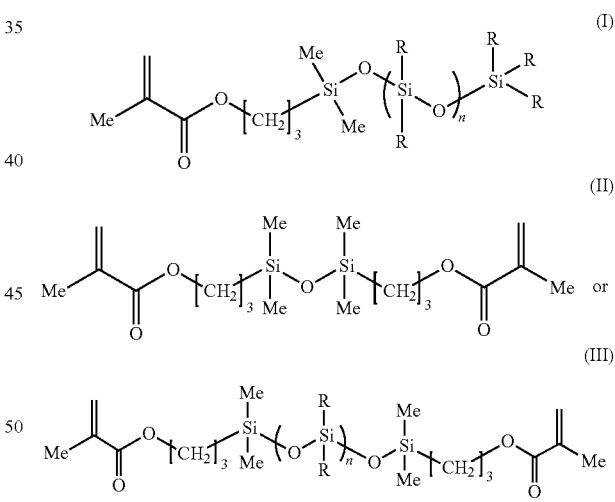

in which n is 0 to 100, and each R independently is a $C_{1-4}$alkyl group, especially a methyl group, by known methods. For example, it may be reacted with a (poly)siloxane of the formula (IV):

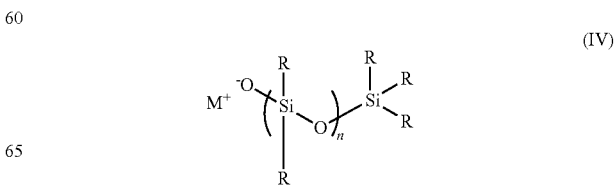

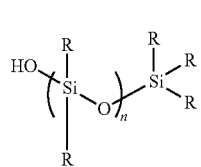
(IVa)

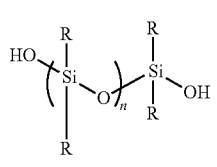
(Va)

in which M⁺ is a cation, for example a metal ion, especially a lithium ion, to form a compound of formula (I).

Specific examples of compounds of formula (I) include:

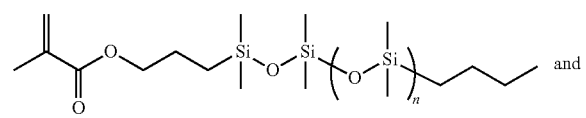
(Ia)

and

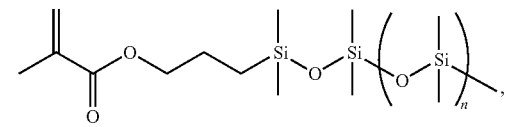
(Ib)

which may for example be produced by a reaction between MOPDMCS and an appropriate compound of formula (IV) or (IVa) as shown below in a reaction scheme using a lithium salt of formula (IV):

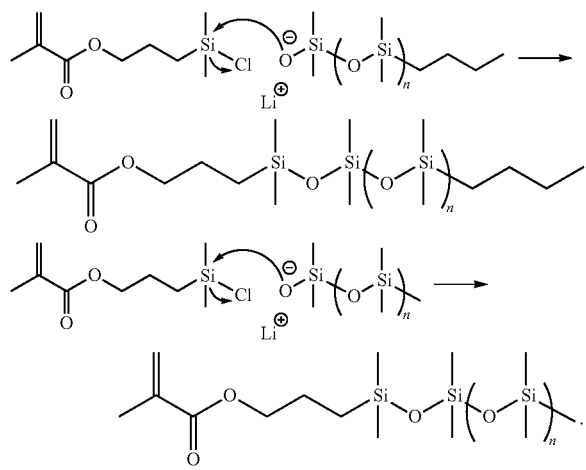

Two molecules of MOPDMCS may be dimerised in the presence of water to form a compound of formula (II), or two molecules of MOPDMCS may be reacted with a compound of formula (V) or (Va):

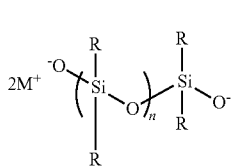
(V)

in which M⁺ has the meaning given above, to form a compound of the formula III.

The process of the present disclosure is a process for the preparation of MOPDMCS which provides a significant improvement compared with known processes, specifically providing a significant improvement in the quality and consistency of the product, as well as leading to an improvement in overall yields. The results obtained using the process of the present disclosure are surprisingly rapid, consistent and controllable. The skilled man would have expected deposition of solid polymer to occur within the continuous flow reactor, making the use of a continuous flow reactor not feasible given the nature of the reaction, but in fact, as demonstrated in the Example below, this does not occur. Further, given the fact that in known ways of carrying out the reaction there is a significant induction time during which catalyst activation must be allowed to occur before initiating the reaction, it is most surprising that no allowance for induction period needs to be made when carrying out the process of the present disclosure, and that high yields can be obtained with low residence time. The reaction is sensitive to the presence of water, which causes impurities in the product. The process of the present disclosure permits the use of apparatus in which the number of points of ingress for water is low, and the surface area of wettable surfaces within the apparatus is also low. Finally, it is surprising that the reaction takes place efficiently without significant catalyst deactivation without taking any active steps to introduce a source of oxygen, for example peroxide, into the system, it previously having been believed that a source of oxygen was necessary to avoid catalyst deactivation.

A preferred embodiment of the present disclosure is shown in FIG. 1. In that embodiment, allylmethacrylate, a polymerization inhibitor (e.g. phenothiazine) and hydrosilylation catalyst (e.g. platinum(0)-1,3-divinyl-1,1,3,3-tetramethyldisiloxane in xylenes) is provided to a first storage vessel 1 (indicated as "input A" in FIG. 1). Dimethylchlorosilane is provided to a second storage vessel 2 (indicated as "Input B"). A first stream containing the AMA, polymerization inhibitor and hydrosilylation catalyst is pumped from the first storage vessel and is combined with a second stream containing the DMCS and the combined stream is flowed immediately into a continuous flow reactor 3 at a temperature in the range of from 80 to 100° C. The flow rate of the first and second streams is adjusted so as to achieve a residence time of the reactants in the continuous flow reactor in the range of from 1 to 5 minutes, and to achieve a pressure in the range of from 500 to 1500 kilopascals. The DMCS reacts with the AMA, and a crude product stream containing the MOPDMCS exits the continuous flow reactor. The crude product stream is subjected to in-line analysis by passing it through an in-line IR instrument 4 equipped with a silicon probe. Where analysis confirms that the crude product stream contains MOPDMCS in acceptable yield and purity, the crude product stream is allowed to pass via valve 5 to distillation column 6 where the crude product stream is subject to distillation, providing the purified MOPDMCS (indicated as "output" in FIG. 1) and a waste stream. Where in-line IR analysis indicates that the crude product stream is not of acceptable yield and/or purity (for example where polymerization of the AMA or MOPDMCS starts to take place), the crude product stream is diverted via valve 5 to waste preventing spoiling of the product stream. A third stream containing solvent (e.g. toluene, xylenes) and polymerization inhibitor (e.g. phenothiazine) introduced to a third storage vessel 7 (indicated as "Input C" in FIG. 1) is then pumped from the vessel 7 through the continuous flow reactor 3 for a period of time in place of the first and second streams, purging the reactor. Normal operation is then resumed, with first and second streams being contacted in the continuous flow reactor 3 to produce further methacyloyl-organosilicon compound, and where in-line IR analysis indicates that the crude product stream is once again of acceptable yield and/or purity, the crude product stream is again allowed to pass via valve 5 to distillation column 6.

The following Examples illustrate embodiments of the present disclosure.

Example 1: Continuous Preparation of MOPDMCS

A solution of phenothiazine (0.28 g, 1.41 mmol), allylmethacrylate (60 mL, 446 mmol), and platinum(0)-1,3-divinyl-1,1,3,3-tetramethyldisiloxane complex solution (2% Pt in xylenes, 66 μL, 20 ppm Pt) was prepared in a dry, sealed 100 mL round bottomed flask under an atmosphere of $N_2$. A peristaltic pump-equipped Vapourtec® E-Series flow reactor having a surface area/volume ration of 40:1 was used to carry out the reaction. The solution of phenothiazine and platinum(0)-1,3-divinyl-1,1,3,3-tetramethyldisiloxane complex solution was pumped using a first peristaltic pump at a rate of 1.1 mL min$_{-1}$ to a PTFE t-piece, where it was combined with a stream of dimethylchlorosilane being pumped at a rate of 0.9 mLmin$_{-1}$ using a second peristaltic pump. The combined stream was flowed immediately into a 10 mL tubular reactor, which was being held at 80° C., the system kept under pressure by means of a 100 PSI back-pressure regulator. The output stream of the system was passed through a Mettler-Toledo® FlowIR in-line FTIR instrument equipped with a silicon probe, which confirmed the complete consumption of all hydrosilane species. IR monitoring also confirmed consistent product production over the course of the experiment. The output stream was flowed into a waste receptacle for 10 minutes before being diverted to a dry, sealed 100 mL round bottomed flask under an atmosphere of $N_2$ for 30 min. BHT (butylated hydroxyl toluene) (13.7 mg, 250 ppm) was charged to the solution and the solution was stripped in vacuo at 80° C. for one hour to give MOPDMCS (47.9 g, 97.9% yield) as a pale yellow liquid shown by GC to be of 89% purity.

Comparative Example 1: Batch Preparation of MOPDMCS

A 2 L reaction kettle was fitted with a mechanical stirrer, condenser, thermocouple, air sparge, sub-surface water cooling coil, 500 mL dropping funnel, heating mantle, $N_2$ inlet and $N_2$ bubbler. To the kettle was charged phenothiazine (0.93 g, 4.7 mmol), allyl methacrylate (146 mL, 1.09 mol), toluene (340 mL) and platinum(0)-1,3-divinyl-1,1,3,3-tetramethyldisiloxane complex solution (2% Pt in xylene solution, 137 μL, 20 ppm Pt) and the contents were stirred for 10 min. The solution was heated to 80° C. and a solution of dimethylchlorosilane (94 mL, 0.85 mol) in toluene (200 mL) charged to a dropping funnel. Approximately 30 mL (10%) of the dimethylchlorosilane solution was charged to the kettle and the kettle was held at 80° C. for 30 min. The contents of the kettle were sampled at this time and after approx. 30 min, confirmation of reaction turnover was obtained from GC-FID analysis. The remaining DMCS solution was added drop wise over a time period of 3 hours to the kettle with maintained temperature and stirring. The reaction was highly exothermic. Excessive increase in the temperature of the reaction had to be controlled by using the cooling coil. After the addition of DMCS was complete, the solution was heated and stirred for a further 1 hour and then allowed to cool to room temperature. BHT (butylated hydroxyl toluene) (47 mg, 250 ppm) was charged to the solution and the solution was stripped in vacuo at 80° C. for one hour to give MOPDMCS (144 g, 77% yield) as a pale yellow liquid shown by GC to be of 88% purity.

Example 2: Continuous Preparation of MOPDMCS

A continuous flow reaction was executed using a Plantrix (Trade Mark) MR260 reactor fitted with three SiC modules (MRX+MRH-II+MRH-II, giving a total reaction volume of 69.9 ml) with Ti connectors & bushings. The reactor was maintained at 7 bar using a back pressure regulator at the reactor outlet to allow the use of high temperatures. Pressure safety relief valves were fitted on each reagent inlet at 17 bar to protect the system from over-pressurisation. A handheld pressure gauge was fitted to the AMA feedline to measure the pressure drop within the reactor under the reaction conditions. Reagents were dosed from 1000 ml (DMCS) and 2500 ml (AMA) glass bottles maintained under 0.5 to 0.7 bar of $N_2$ to aid smooth reagent dosing. The reagents were pumped using a pair of dual syringe pumps fitted with 25 ml PTFE-lined syringes and PEEK check valves (KiloFlow®). The reaction products were cooled in a FEP tube submerged in a salt/ice bath ahead of passing through the back pressure regulator and into a Mettler-Toledo® FlowIR in-line FTIR instrument equipped with a silicon probe. The reactor temperature was thermally controlled using a Lauda XT150 thermostat (Kryo 55 thermal fluid).

The total system was tested with laboratory grade THF and flushed with anhydrous THF prior to employing the pure reagents in a reaction. The reactor was then heated up in intervals from 40° C. to 70° C. to 90° C., with DMCS introduced at 70° C. On detection of the Si—H stretch by IR, the AMA feed, with 20 ppm Pt (Karstedt's catalyst) with respect to AMA and 5000 ppm BHT with respect to the product MOPDMCS, was started. The molar ratio of AMA to DMCS was 1.1:1, residence time in the reactor was 2 minutes, and the stable pressure in the reactor was 9.4 bar.

Following the reduction in the Si—H stretch the reactor temperature was increased to 90° C. and after equilibration (three system volumes) the reaction product was collected into 1 L bottles on ice. During continuous operation a faint yellow, low viscosity product was obtained, no pressure increases or polymer products were formed and the reactor was able to be operated for in excess of 5 hours without problem. The resulting reaction product was analysed by GC-FID (72.4% MOPDMCS) and stored in a refrigerator with all bottles fitted with a vented cap.

The reaction was repeated using 5270 ppm BHT with respect to the product MOPDMCS. Again stable operation was observed with good product conversion. All the MOPDMCS product remained stable after overnight storage with minimal signs of venting. After collection, the crude MOPDMCS produced was distilled to improve its purity.

Example 3: Demonstration of the Relative Stability to Polymerisation of MOPDMCS and MOPTMOS 15 g of MOPTMOS (3-(trimethoxysilyl)propyl methacrylate), containing 500 ppm BHT as stabiliser, was stirred at 100 rpm and heated for 2 hours at 130° C. and then the temperature increased to 135° C. After 7 hours 5 minutes (i.e. after 5 hours 5 minutes at 135° C.), the MOPTMOS polymerised. In contrast, when the experiment was repeated using MOPDMCS with the same amount of BHT, polymerisation occurred after only 2 hours 45 minutes (i.e. within 45 minutes at 135° C.).

Example 4: Effect of Catalyst Concentration

Continuous flow reactions utilising various catalyst loadings were executed using a Vapourtec E-series flow reactor fitted with a standard 10 ml PFA coiled tube reactor and V3 peristaltic pumps. The reactor was maintained at 5-6 bar using a back pressure regulator at the reactor outlet to allow the use of high temperatures. Reagents were dosed using acid resistant flanged tubing from glass bottles maintained under a $N_2$ headspace.

The system was flushed with anhydrous toluene prior to employing the pure reagents. The reactor was then heated to 80° C. One system volume of DMCS was pumped through the system before introducing the AMA feed. The AMA feed contained 20 ppm Pt (Karstedt's catalyst) with respect to AMA and 1000 ppm BHT with respect to the product MOPDMCS. The molar ratio of AMA to DMCS was 1:1, residence time in the reactor was 5 minutes, and the stable pressure in the reactor was 5-6 bar. After equilibration (three system volumes) the reaction product was collected into glass bottles for 15 minutes. During continuous operation the product appeared as a faint yellow, low viscosity product, no pressure increases or polymer products were formed. The product was analysed by GC-FID (72.1% MOPDMCS) and stored cold.

The reaction was repeated with AMA feeds containing different levels of Karstedt's catalyst (15 ppm, 10 ppm and 5 ppm Pt). The inhibitor content, equipment and reaction conditions were unchanged. Stable operation at 5-6 bar was observed and pale yellow, low viscosity products were collected with no polymer products formed. GC-FID analysis of all MOPDMCS products showed good product conversion for each catalyst loading. The purity measured for 15 ppm Pt, 10 ppm Pt and 5 ppm Pt were 68.8% MOPDMCS, 69.2% MOPDMCS and 70.5% MOPDMCS respectively.

The invention claimed is:

1. A process for the preparation of 3-methacryloxypropyldimethylchlorosilane by reaction of allylmethacrylate with dimethylchlorosilane in the presence of a hydrosilylation catalyst, wherein the reaction is carried out in the absence of a peroxide by the process comprising:
   i) providing a first stream containing allylmethacrylate;
   ii) providing a second stream containing dimethylchlorosilane;
   iii) contacting said streams in a single pass continuous flow reactor in the presence of said hydrosilylation catalyst, thereby producing 3-methacryloxypropyldimethylchlorosilane; and
   iv) continuously removing a product stream from said single pass continuous flow reactor.

2. The process as claimed in claim 1, wherein the surface area/volume ratio of the single pass continuous flow reactor is in the range of from 4:1 to 400:1.

3. The process as claimed in claim 1 wherein, the ratio of the cross sectional area of the single pass continuous flow reactor to the path length of the reagents in the single pass continuous flow reactor is in the range of from 0.01:10,000 to 100:10,000.

4. The process as claimed in claim 1, wherein the process is carried out in the absence or substantial absence of solvent.

5. The process as claimed in claim 1, wherein in-line analysis of the product stream produced in step (iii) is carried out.

6. The process as claimed in claim 5, in which the in-line analysis is carried out by HPLC, GC-FID, GC-MS or IR.

7. The process as claimed in claim 5, further comprising determining the purity and/or yield of 3-methacryloxypropyldimethylchlorosilane present in the product stream and, where the purity and/or yield of 3-methacryloxypropyldimethylchlorosilane is equal to or greater than a pre-defined value, passing the product stream to a first vessel; or, where the purity and/or yield of 3-methacryloxypropyldimethylchlorosilane is less than said predefined value, passing the crude product stream to a second waste vessel.

8. The process as claimed in claim 1, wherein the first and second streams are provided to the single pass continuous flow reactor at a flow rate such that they are contacted in the single pass continuous flow reactor at a pressure in the range of from 100 to 10,000 kilopascals.

9. The process as claimed in claim 1, wherein step (iii) as carried out at temperature in the range of from 30 to 120° C.

10. The process as claimed in claim 1, wherein the hydrosilation catalyst contains rhodium or platinum.

11. The process as claimed in claim 10, wherein the catalyst is the reaction product of $H_2PtCl_6$ and divinyltetramethyldisiloxane.

12. The process as claimed in claim 1, wherein step (iii) is carried out in the presence of an inhibitor.

13. The process as claimed in claim 12, wherein the inhibitor is phenothiazine and/or bis(tert butyl)-4-methylphenol.

14. A process as claimed in claim 1, further comprising an additional step v) which comprises subjecting the product stream from step iv) to batch distillation.

15. The process as claimed in claim 1, further comprising converting 3-methacryloxypropyldimethylchlorosilane to a compound of the general formula:

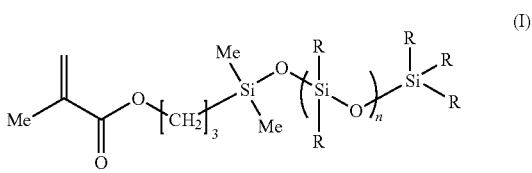

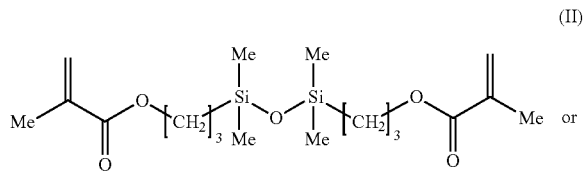

(III)

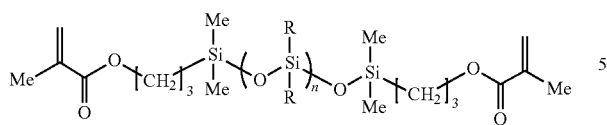

in which n is 0 to 100, and each R independently is a $C_{1-4}$alkyl group.

16. The process as claimed in claim 15, wherein converting comprises reacting 3-methacryloxypropyldimethylchlorosilane with a (poly)siloxane of the formula:

(IV)

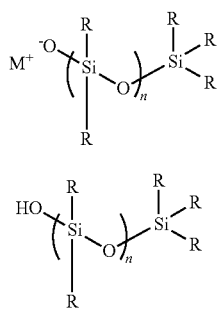

(IVa)

in which M+ is a cation, to form a compound of formula (I); or dimerising two molecules of 3-methacryloxypropyldimethylchlorosilane in the presence of water to form a compound of formula (II); or reacting two molecules of 3-methacryloxypropyldimethylchlorosilane with a compound of formula:

(V)

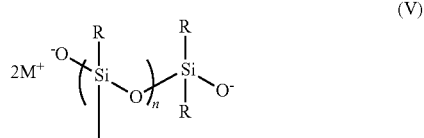

(Va)

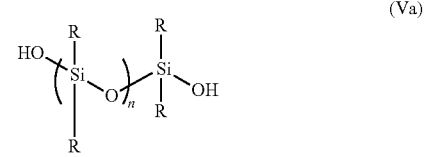

in which $M^+$ is a cation, to form a compound of the formula III.

17. The process as claimed in claim 2, wherein the ratio of the cross sectional area of the single pass continuous flow reactor to the path length of the reagents in the single pass continuous flow reactor is in the range of from 0.01:10,000 to 100:10,000.

18. The process as claimed in claim 6, further comprising determining the purity and/or yield of 3-methacryloxypropyldimethylchlorosilane present in the product stream and, where the purity and/or yield of 3-methacryloxypropyldimethylchlorosilane is equal to or greater than a pre-defined value, passing the product stream to a first vessel; or, where the purity and/or yield of 3-methacryloxypropyldimethylchlorosilane is less than said pre-defined value, passing the crude product stream to a second waste vessel.

* * * * *